US010391024B2

(12) United States Patent
Cambridge

(10) Patent No.: US 10,391,024 B2
(45) Date of Patent: Aug. 27, 2019

(54) DEVICE FOR CREATING THE ILLUSION OF PENETRATION

(71) Applicant: THIKA HOLDINGS LLC, St. Pete Beach, FL (US)

(72) Inventor: Vivien Johan Cambridge, Myrtle Beach, SC (US)

(73) Assignee: THIKA HOLDINGS LLC, St. Pete Beach, FL (US)

( * ) Notice: Subject to any disclaimer, the term of this patent is extended or adjusted under 35 U.S.C. 154(b) by 504 days.

(21) Appl. No.: 15/174,327

(22) Filed: Jun. 6, 2016

(65) Prior Publication Data

US 2016/0354278 A1 Dec. 8, 2016

Related U.S. Application Data

(60) Provisional application No. 62/172,068, filed on Jun. 6, 2015.

(51) Int. Cl.
*A61F 5/00* (2006.01)
*A61H 19/00* (2006.01)

(52) U.S. Cl.
CPC ..... *A61H 19/44* (2013.01); *A61H 2201/1664* (2013.01)

(58) Field of Classification Search
CPC ........ A61H 19/00; A61H 19/30; A61H 19/34; A61H 19/40; A61H 19/44
USPC ...................................................... 600/38–41
See application file for complete search history.

(56) References Cited

U.S. PATENT DOCUMENTS 6,251,066 B1 6/2001 Pack
6,632,185 B2 10/2003 Chen

FOREIGN PATENT DOCUMENTS

DE 102011013729 A1 9/2012
GB 2461010 A 12/2009
GB 2482963 A 2/2012

*Primary Examiner* — John P Lacyk
(74) *Attorney, Agent, or Firm* — Volpe and Koenig, P.C.

(57) ABSTRACT

A sex toy having an initial, extended state, wherein the sex toy has a first longitudinal length, and a secondary, compressed state, wherein the sex toy has a second longitudinal length that is less than the first longitudinal length. A concentrically arranged tube and a rod are provided within a housing of the sex toy, and a spring expands the sex toy to the initial extended state. The spring is compressed and the rod slides within the tube in the secondary, compressed state.

12 Claims, 4 Drawing Sheets

DEVICE FOR CREATING THE ILLUSION OF PENETRATION

CROSS REFERENCE TO RELATED APPLICATIONS

This application claims the benefit of U.S. provisional patent application 62/172,068, filed on Jun. 6, 2015, which is incorporated by reference as if fully set forth.

FIELD OF INVENTION

The present application is generally related to a sexual device, and more specifically, to a sexual device that simulates the appearance of penetration.

BACKGROUND

One type of adult entertainment services involves entertainers showing various erotic acts over the Internet. The entertainer typically has a webcam that transmits a video stream through the entertainer's computer to a user's computer over the Internet. The entertainer typically performs various sexual acts that are meant to arouse the user. One of the acts performed by the entertainer includes insertion of a sexual toy into an orifice of the entertainer. Based on a user's requests or volume of business, this insertion can be repeated frequently each day for extended periods of time. This frequent and repeated insertion can be detrimental to the health of the entertainer. The repetitive insertion can cause infections, irritation, and/or various other undesirable side effects. A need exists for a way to reduce the amount and degree of insertion of the sexual toys for an entertainer while still satisfying a user's requests.

SUMMARY

The present invention includes a sex toy that simulates insertion of the sex toy while minimizing the degree of insertion of the sex toy into a user.

In one embodiment, a device for simulating penetration into a body orifice is disclosed. The device includes a collapsible body having a first expanded state and a second compressed state.

In another embodiment, a sex toy is disclosed that creates the illusion of insertion as the sex toy collapses along its longitudinal axis. According to the present invention, a first end of the sex toy includes a tip dimensioned for insertion into an orifice of a user. A second end of the sex toy includes a base that is configured to be pushed by the user to force the sex toy into the user's orifice. As the user pushes the base of the sex toy towards the user's orifice, the sex toy collapses upon itself due to concentric tubes within an elastic body of the sex toy. A length of the sex toy is shortened corresponding to the degree of movement that the base of the sex toy is pushed towards the user's orifice. The tip remains near the user's orifice regardless of how much pressure the user applies to the sex toy. As the user releases the pressure on the base of the sex toy, the sex toy then elongates, or decompresses, and the base of the sex toy moves away from the user's orifice. This creates the illusion that the sex toy is being extracted from the user's orifice. The present invention then allows performers in erotic video shows to create a convincing illusion of penetrative masturbation even when the invasion of the body cavities with foreign objects is limited.

DETAILED DESCRIPTION OF THE PREFERRED EMBODIMENTS

Figure 1:
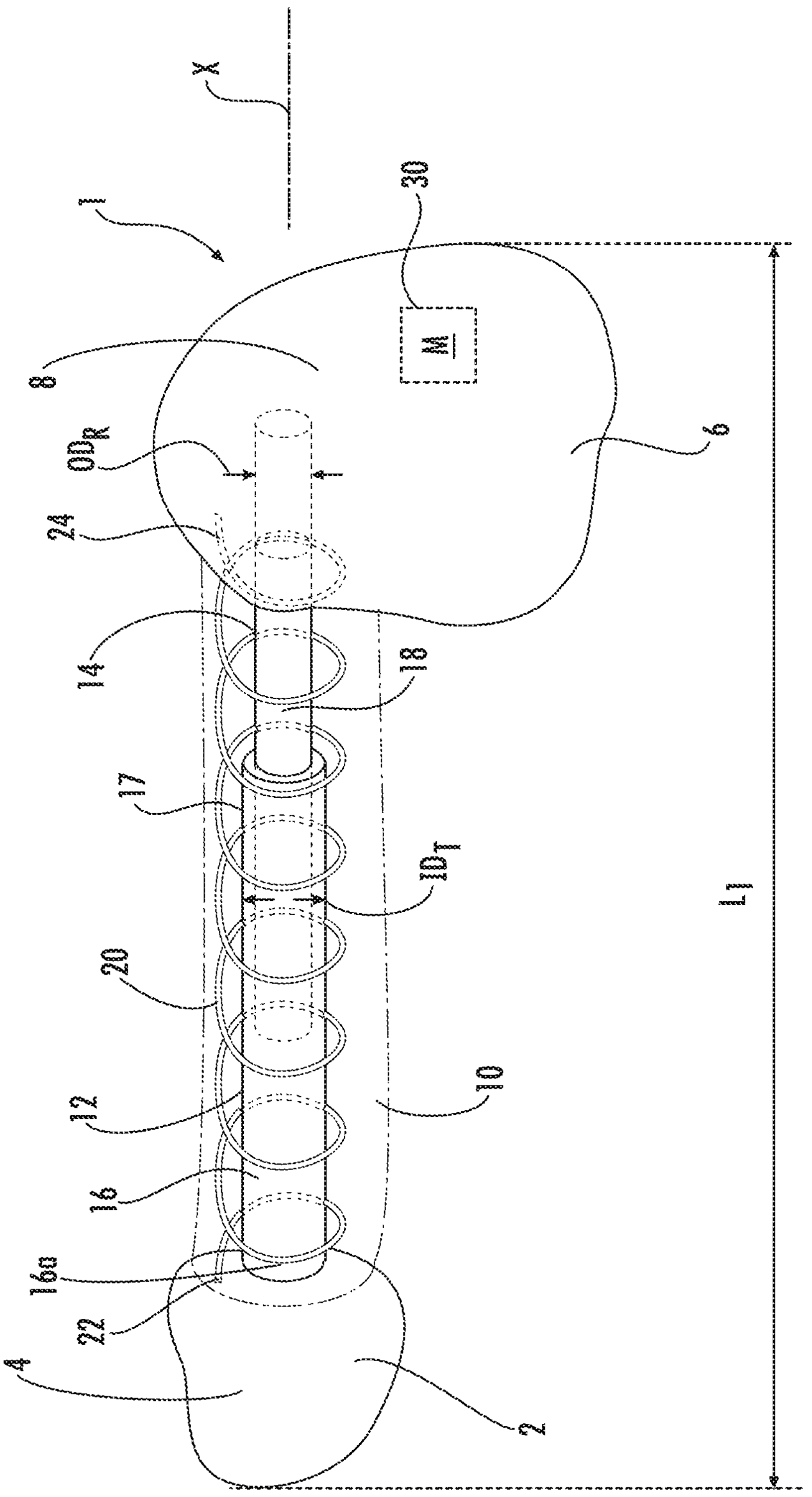
FIG. 1 is a cross-sectional view of a sex toy according to an embodiment of the invention in an initial state.

FIG. 1 shows a sexual masturbation device, such as a sex toy 1 according to an embodiment of the present invention. The sex toy 1, which may preferably be shaped to resemble a male member, includes a first end 2 comprising a tip 4. The tip 4 is preferably shaped and dimensioned to resemble, for example, the tip of a penis. It is appreciated that the sex toy 1 can have any shape, and that those in the art will appreciate that masturbation devices, such as dildos, have many shapes. The sex toy 1 includes a second end 6 comprising a base 8. The base 8 is preferably larger than the tip 4. The sex toy includes a housing 10 connecting the tip 4 to the base 8. The housing 10 is preferably a sleeve preferably formed from an elastic material that can be deformed and manipulated by a user. The tip 4 preferably has a larger outer diameter than an outer diameter of the housing 10. The housing 10 is preferably formed from a more elastic and more deformable material compared to a material used to form the tip 4 and the base 8.

The tip 4 is preferably connected to the housing 10, and the base 8 is preferably connected to the housing 10. Within the housing 10, the sex toy 1 includes at least two concentrically arranged elongated cylinders 12, 14. In one embodiment, a first one of the cylinders 12 includes a tube 16. The tube 16 has a first end **16*a* that abuts an internal surface of the tip 4 or is fixed to the internal surface of the tip 4. As shown in FIG. 1, the tube 16 has an internal bore 17 with an internal diameter ($ID_T$) that is dimensioned to accommodate a second one of the cylinders 14. The second one of the cylinders 14 preferably comprises a rod 18. The rod 18 is preferably fixed to the base 8 at one end. An outer diameter ($OD_R$) of the rod 18 is less than the internal diameter ($ID_T$) of the bore 17 of the tube 16 such that a clearance is provided between the tube 16 and the rod 18. When pressure is applied to the sex toy 1, the tube 16 slides along a longitudinal axis (X) of the sex toy 1 to allow the tube 16 to slide over the rod 18. The sleeve 10** will flex as the tubes slide relative to each other.

A spring 20 is arranged within the housing 10 configured to bias the tip 4 to a first position, or initial state. A first spring end 22 is engaged against the tip 4 and a second spring end 24 is engaged against the base 8. The spring 20 extends along the longitudinal axis (X) of the sex toy 1. In an embodiment, the spring 20 is arranged concentrically about the tube 16 and the rod 18. In another arrangement, the spring 20 can be positioned at another location, so long as the spring 20 biases the tip 4 to a first position or initial state, such that the housing 10 is in an extended state. In an initial state shown in FIG. 1, the spring 20 provides a biasing force that keeps the housing 10 in a fully extended or "non-flexed" position. In the initial state, the rod 18 is at a most extended state within the tube 16 and the sex toy 1 has a first longitudinal length ($L_1$). The spring 20 preferably has a stiffness or strength that ensures the tip 4 is maintained in an extended position with respect to the base 8 in the initial state. The spring 20 ensures that the sex toy 1 extends in a straight line along its longitudinal axis (X). In this initial state, the spring 20 is in an extended state and only a portion, i.e. less than 50%, of the rod 18, is arranged within the tube 16. The rod 18 preferably extends into the base 8 such that the rod 18 is anchored within the base 8, which provide stability and helps prevent the spring 20 from kinking.

Figure 2:
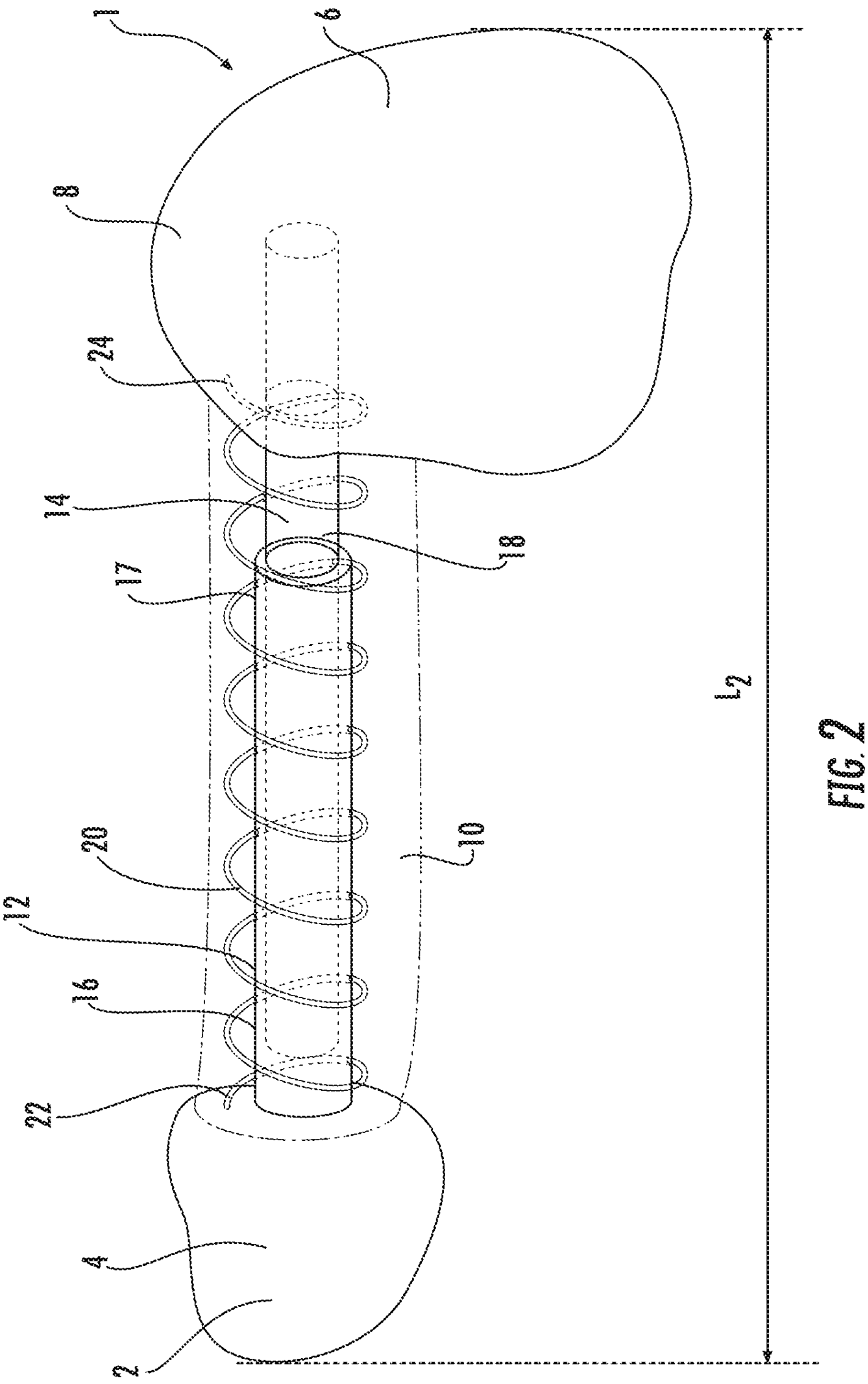
FIG. 2 is a cross-sectional view of the sex toy of FIG. 1 in a secondary, compressed state.

In a secondary state or "flexed" state shown in FIG. 2, when a user pushes the sex toy 1 towards the user's orifice, the tip 4 is dimensioned to remain adjacent to the user' orifice as the user pushes the base 8 towards the user's orifice. This state corresponds to a compressed or collapsed state. The rod 18 slides within the tube 16 as more pressure is applied to the base 8 of the sex toy 1. Instead of the tip 4 being forced into the user and beyond the user's orifice, the sex toy 1 collapses upon its longitudinal axis (X) due to the rod 18 sliding within the tube 16. In this secondary state, a second longitudinal length ($L_2$) of the sex toy 1 is reduced, and the spring 20 is compressed. The second longitudinal length ($L_2$) is less than the first longitudinal length ($L_1$). In the secondary state, a majority of the rod 18, i.e. more than 50% of the rod 18, is arranged within the tube 16. The housing 10 compresses with the movement between the initial state and secondary state in a way that is not perceptible or only slightly perceptible by an observer. The housing 10 is formed from a highly elastic material, such as a rubber or elastomer or neoprene, and the material is selected so that it does not show significant folding, wrinkling or bunching when the housing 10 is compressed in the secondary state. As the base 8 of the sex toy 1 is moved in an opposite direction from the user's orifice, the sex toy 1 returns to the initial state and the housing 10 expands due to the spring 20 returning to its extended state. As the base 8 of the sex toy 1 is moved away from the user's orifice, the rod 18 slides out of the tube 16 back to the initial state positions. As the sex toy 1 is moved back and forth from with respect to a user's orifice, a length of the sex toy 1 is changing, however it appears to an external viewer that the sex toy 1 is being inserted into the user's orifice. The dimensions of the tip 4, the base 8, the tube 16, and the rod 18 remain constant between the initial state and secondary state. Only the housing 10 and the spring 20 experience changes in dimensions during movement between the initial state and the secondary state.

In FIGS. 1 and 2, the tube 16 is shown as being adjacent to the tip 4 and the rod 18 is arranged adjacent to the base 8. One of ordinary skill in the art recognizes that this arrangement could be reversed such that the rod 18 is arranged adjacent to the tip 4 and the tube 16 is arranged adjacent to the base 8. One of ordinary skill in the art would recognize from the above description that other types of arrangements could be used to provide the telescoping movement of the tube 16 and the rod 18. Multiple telescoping rods and tubes could be used. In another embodiment, a motor 30 (shown schematically in FIG. 1) can be provided to automatically drive the compression and extension of the sex toy between the initial state and secondary state. The motor 30 can be controlled by the user to adjust the extension and compression of the sex toy 1.

Figure 3:
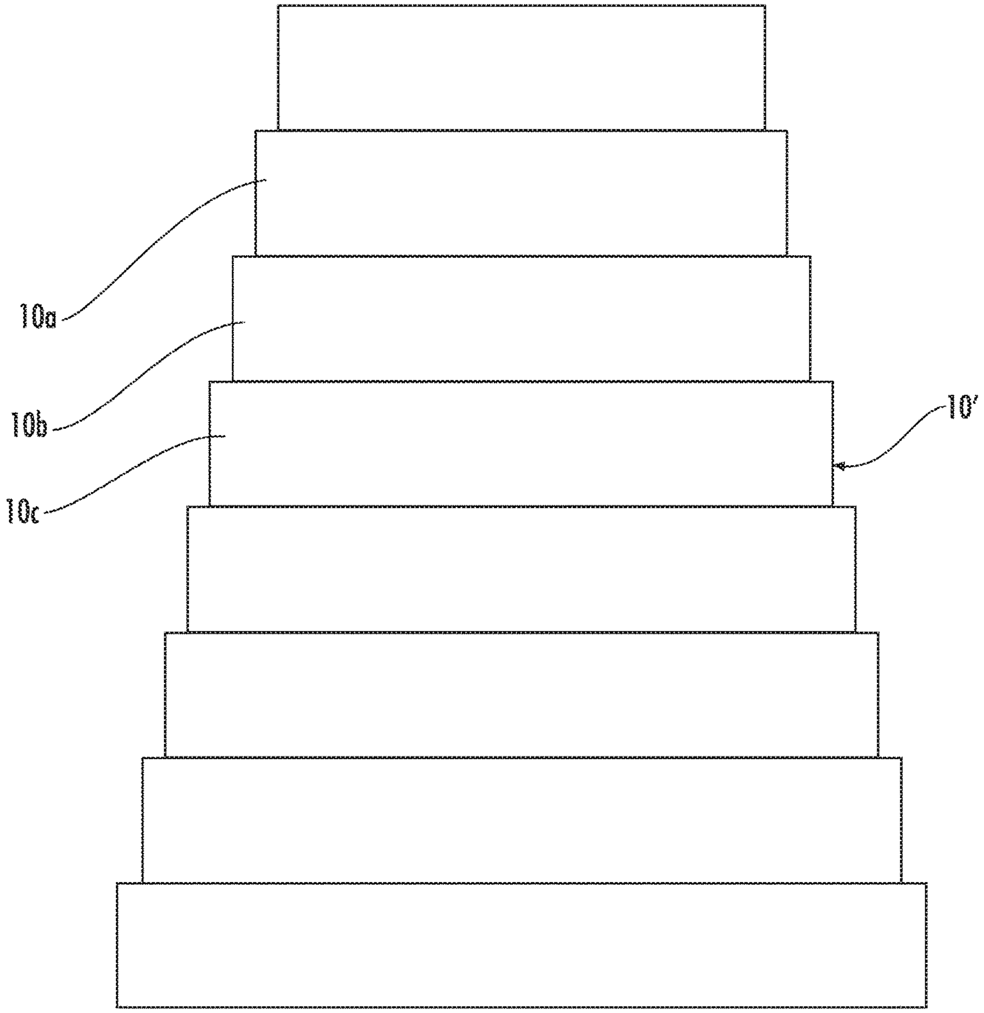
FIG. 3 is a schematic view of a housing for a sex toy according to the invention.

FIG. 3 illustrates an alternative embodiment of a housing 10' for a sex toy 1 described above. In this embodiment, the housing 10' includes a segmented or modular configuration with a plurality of portions 10*a*, 10*b*, 10*c*. The portions 10*a*, 10*b*, 10*c* each have a constant outer diameter that is different than an adjacent portion's outer diameter. The portions 10*a*, 10*b*, 10*c* allow the housing 10' to be collapsed via the portions 10*a*, 10*b*, 10*c* partially or completely nesting within one another. This arrangement provides the same benefits described above with respect to the housing 10 compressing when the sex toy 1 is pushed against an object.

In another embodiment, the tube 16 and the rod 18 can be omitted and the spring 20 can provide a sufficient biasing force in the initial state that the sex toy extends straight along its longitudinal axis (X). In this embodiment, the function of the sex toy 1 is identical as described above.

In another embodiment, a central plate can be provided in a mid-portion of the housing 10. The central plate can include two opposing springs, a first one engaging between the central plate and the tip 4 and a second one engaging between the central plate and the base 8.

Figure 4:
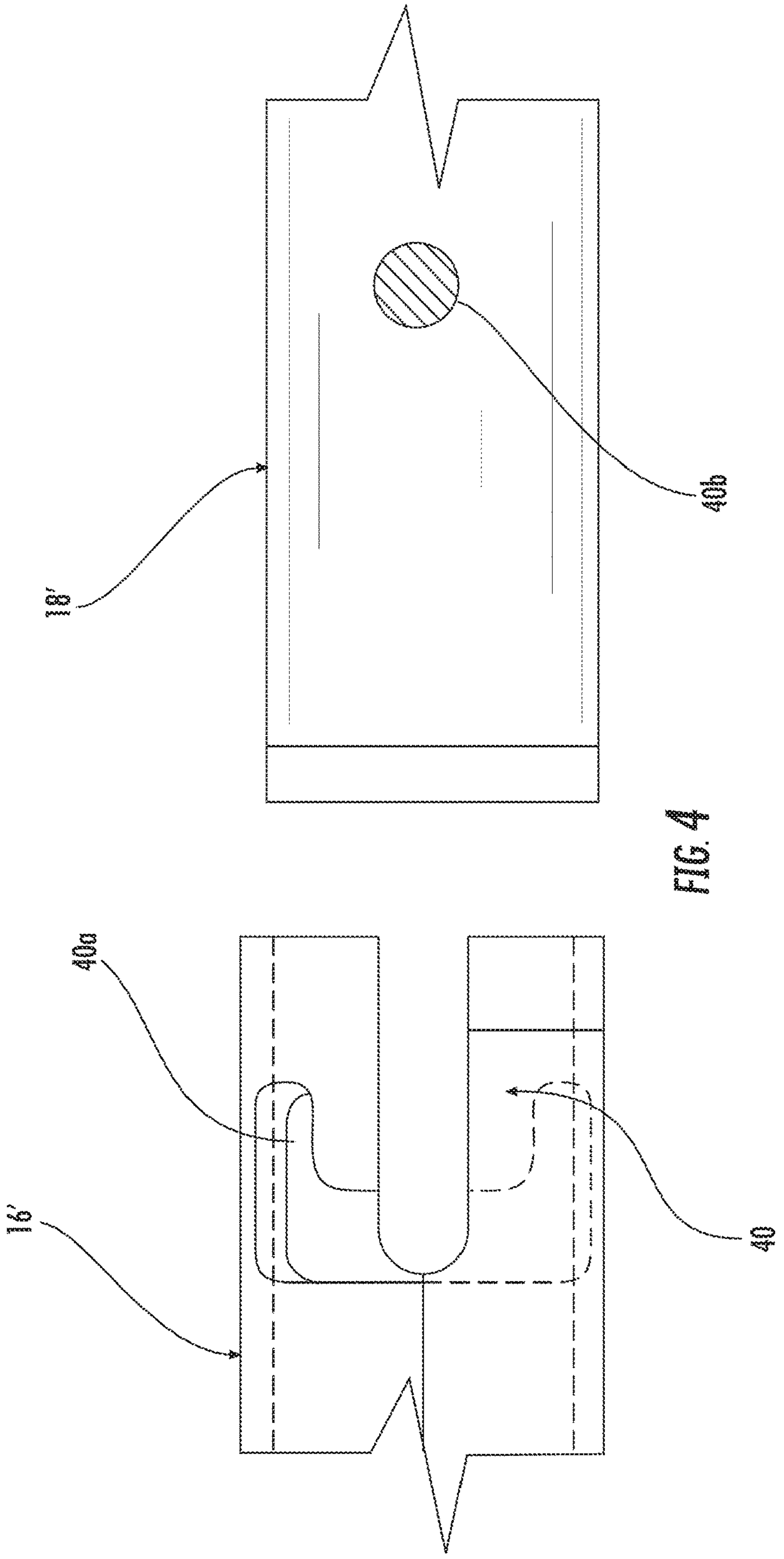
FIG. 4 is a magnified view of a lock for a sex toy according to the invention.

In another embodiment, the sex toy 1 can be locked in the extended, first initial state in which the housing 10 is extended. The sex toy 1 can be locked in the fully extended position by a locking mechanism 40, such as illustrated in FIG. 4. The locking mechanism 40 shown in FIG. 4 is a bayonet-type connection, which is provided for illustration. By inserting the pin 40*b* of the rod 18' into the slot 40*a* in the tube 16', and turning the housing 10, the housing 10 can be locked in the extended, first initial state. One of ordinary skill in the art will recognize that a wide range of locking mechanisms or arrangements could be used, such as a locking pin or latch, bayonet connection, friction coupling, threaded connection, or any other known locking arrangement. A twisting lock configuration could also be provided. In one embodiment, the spring 20 can provide a biasing force that maintains the sex toy 1 in the locked state. Any one of these known locking mechanisms or configurations can be configured to engage, for example, the tube 16 and the rod 18 in a locked position. The locking mechanism 40 could also be provided between any other components of the sex toy 1 in order to maintain the housing 10 in the extended, first initial state. This provides for a convertible sex toy device that can be used as, for example, a non-collapsible dildo, and a device providing for the simulation of penetration as described herein.

It will be appreciated that the foregoing is presented by way of illustration only and not by way of any limitation. It is contemplated that various alternatives and modifications may be made to the described embodiments without departing from the spirit and scope of the invention. Having thus described the present invention in detail, it is to be appreciated and will be apparent to those skilled in the art that many physical changes, only a few of which are exemplified in the detailed description of the invention, could be made without altering the inventive concepts and principles embodied therein. It is also to be appreciated that numerous embodiments incorporating only part of the preferred embodiment are possible which do not alter, with respect to those parts, the inventive concepts and principles embodied therein. The present embodiment and optional configurations are therefore to be considered in all respects as exemplary and/or illustrative and not restrictive, the scope of the invention being indicated by the appended claims rather than by the foregoing description, and all alternate embodiments and changes to this embodiment which come within the meaning and range of equivalency of said claims are therefore to be embraced therein.

What is claimed is:

1. A sex toy comprising:

an elastic housing connected to a tip at a first end and a base at a second end; and a spring arranged within the elastic housing with a first spring end engaged against the tip and a second spring end engaged against the base;

wherein (1) in an initial state, the spring is configured to be in an extended state, and in such initial state the sex toy has a first longitudinal length, and (2) in a secondary state, the spring is configured to be compressed within the housing along a longitudinal axis (X) such that the elastic housing compresses and the sex toy is compressed to a second longitudinal length that is less than the first longitudinal length in response to the tip engaging against a user's body to thereby apply pressure to the sex toy.

2. The sex toy of claim 1, further comprising a tube arranged adjacent to the tip within the elastic housing, and a rod arranged adjacent to the base within the elastic housing, wherein a portion of the rod is arranged concentrically within the tube, and the rod slides within the tube in the secondary state.

3. The sex toy of claim 2, wherein the spring is arranged concentric about the tube and the rod.

4. The sex toy of claim 2, wherein in the initial state, a minority of the rod is arranged within the tube.

5. The sex toy of claim 2, wherein in the secondary state, a majority of the rod is arranged within the tube.

6. The sex toy of claim 1, wherein the elastic housing is formed from a softer, more elastic material than the tip and the base.

7. The sex toy of claim 1, wherein manual pressure from a user drives the sex toy between the initial state and the secondary state.

8. The sex toy of claim 1, further comprising a motor that drives the sex toy between the initial state and the secondary state.

9. A sex toy comprising:

an elastic housing connected to a tip at a first end and a base at a second end;

a spring arranged within the elastic housing with a first spring end engaged against the tip and a second spring end engaged against the base;

a tube arranged adjacent to the tip within the elastic housing; and a rod arranged adjacent to the base within the elastic housing, a portion of the rod is arranged concentrically within the tube, and the rod slides within the tube in the secondary state;

the rod extends into the base such that the rod is anchored within the base, wherein (1) in an initial state, the spring is configured to be in an extended state, and in such initial state the sex toy has a first longitudinal length, and (2) in a secondary state, the spring is configured to be compressed within the housing along a longitudinal axis (X) such that the elastic housing compresses and the sex toy is compressed to a second longitudinal length that is less than the first longitudinal length in response to the tip engaging against a user's body to thereby apply pressure to the sex toy.

10. The sex toy of claim 1, wherein an outer diameter of the tip is greater than an outer diameter of the elastic housing.

11. The sex toy of claim 1, wherein the elastic housing is comprised of a plurality of segments each having a constant outer diameter that is different than an outer diameter of an adjacent segment, and the plurality of segments at least partially nest within each other in the secondary state.

12. The sex toy of claim 1, further comprising a lock that fixes the sex toy in the initial state and prevents the sex toy from being compressed to the secondary state.

* * * * *